United States Patent [19]

Kloog et al.

[11] Patent Number: 5,284,867

[45] Date of Patent: Feb. 8, 1994

[54] NMDA-BLOCKING PHARMACEUTICAL COMPOSITIONS

[75] Inventors: Yoel Kloog, Hertzlyia, Israel; Jeffrey J. Feigenbaum, Chicago, Ill.; Raphael Mechoulam, Jerusalem, Israel; Mordechai Sokolovsky, Tel Aviv, Israel; Simon Benita, Mevasseret Zion, Israel

[73] Assignees: Yissum Research Development Company of the Hebrew University in Jerusalem, Jerusalem; Ramot University, Authority for Applied Research and Industrial Development Ltd., Tel Aviv, both of Israel

[21] Appl. No.: 865,088

[22] Filed: Apr. 8, 1992

Related U.S. Application Data

[63] Continuation of Ser. No. 609,588, Nov. 6, 1990, abandoned.

[30] Foreign Application Priority Data

Nov. 7, 1989 [IL] Israel ........................ 92238

[51] Int. Cl.[5] ............................................ A61K 31/35
[52] U.S. Cl. ................................................... 514/454
[58] Field of Search ......................... 514/454; 549/390

[56] References Cited

U.S. PATENT DOCUMENTS 4,133,819  1/1979  Johnson .
4,179,517 12/1979  Mechoulam et al. .
4,209,520  6/1980  Johnson .
4,876,276 10/1989  Mechoulam et al. .

FOREIGN PATENT DOCUMENTS 2826849 12/1978  Fed. Rep. of Germany .

OTHER PUBLICATIONS

Mechoulam et al., Tetrahedron Asymmetry 1: 315-319 (1990).

Choi, Neuron 1: 623-624 (1988).
Kloog et al., Biochemistry 27: 843-848 (1988).
Mechoulam et al., Experientia 44: 762-764 (1988).
Feigenbaum et al., Pharmacol. Biochem. Behav. 16: 235-240 (1982).

Primary Examiner—Nicky Chan
Attorney, Agent, or Firm—Pennie & Edmonds

[57] ABSTRACT

The use of a compound of the formula:

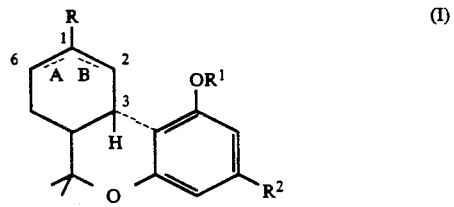

having the (3S,4S) configuration, and which is essentially free of the (3R,4R) enantiomer, wherein A—B designates a 1(2) or a 6(1) double bond, R designates —CH$_3$ or —CH$_2$OH, R$^1$ designates a hydrogen atom or a lower acyl group, and R$^2$ designates (A) a straight-chained or branched C$_{6-12}$ alkyl radical; or (B) a group —O—R$^3$, in which R$^3$ is a straight-chained or branched C$_{5-9}$ alkyl radical or a straight-chained or branched alkyl radical substituted at the terminal carbon atom by a phenyl group in the manufacture of a medicament for reducing or preventing glutamate neurotoxicity. Some of the above compounds are novel, and their preparation is described. Also described is a method of treating acute injuries to the central nervous system associated with excitatory amino acid neurotoxicity, a method of treating chronic degenerative disease associated with gradual selective neuronal loss and a method of treating poisonings affecting the central nervous system by administering a pharmaceutical composition containing the above compound.

18 Claims, 4 Drawing Sheets

NMDA-BLOCKING PHARMACEUTICAL COMPOSITIONS

This application is a continuation of application Ser. No. 07/609,588, filed Nov. 6, 1990, now abandoned.

FIELD OF THE INVENTION

The present invention relates to pharmaceutical compositions for preventing excitatory amino acids neurotoxicity comprising as active ingredient (3S,4S)-tetrahydrocannabinol (THC) type compounds of general formula (I), as hereunder defined.

The compositions of the present invention are particularly effective in alleviating and even preventing glutamate neurotoxicity due to acute injuries to the central nervous system (CNS), such as injuries due to prolonged seizures, compromised or reduced blood supply, deprivation of glucose supply and mechanical trauma. The present compositions may also be effective in alleviating other damages to the CNS like poison-induced convulsions, considered to be associated with amino acids receptors other than that of glutamate, for example glycine.

The compositions of the present invention are also effective in the treatment of certain chronic degenerative diseases which are characterized by gradual selective neuronal loss. In this connection, the compositions of the present invention are contemplated as therapeutically effective in the treatment of the Alzheimer's disease.

The present compositions are of special value in grand mal seizures, global hypoxic ischemic insults, in hypoxia, alone or in combination with blood flow reduction (ischemia) as well as in cases of cardiac arrest and in cases of abrupt occlusion of cerebral arteries (stroke).

Some of the compounds according to formula (I), as will be hereinafter described in detail, are novel compounds and are claimed as such within the scope of the present application.

The active ingredient of the pharmaceutical compositions according to the present invention is a compound of the general formula:

having the (+)—(3S,4S) configuration, wherein A—B designates a 1(2) or a 6(1) double bond, R designates $CH_3$ or $CH_2OH$, $R^1$ designates a hydrogen atom or a lower acyl group, and $R^1$ designates (A) a straight-chained or branched $C_{6-12}$alkyl radical; or (B) a group —O—$R^3$, in which $R^3$ is a straight-chained or branched $C_{5-9}$alkyl radical or a straight-chained or branched alkyl radical substituted at the terminal carbon atom by a phenyl group.

Compounds of formula (I) in which R designates $CH_2OH$ and $R^1$ designates a lower acyl group are novel compounds, claimed herein as such.

BACKGROUND OF THE INVENTION

The review article "Glutamate Neurotoxicity and Diseases of the Nervous System", Neuron, 623-34 (1988) summarizes the present state of knowledge of glutamate neurotoxicity, of the various effects of such toxicity and the various diseases involved. The article describes three kinds of glutamate receptors and summarizes known competitive and noncompetitive blockers of such receptors, providing also a variety of theories on the mechanisms of such activity. According to this article, considerable efforts are being focused on bringing an N-methyl-D-aspartate (NMDA) antagonist to bear on some of the diseases associated with glutamate neurotoxicity. Since no proven effective therapy for neuronal injury, or degeneration, is yet known, and, for example, stroke alone is one of the leading causes of death in many countries, the importance of finding such NMDA antagonist is self-evident. The article states that it will be important to determine whether certain NMDA antagonists are more effective—or have fewer side effects—than others in specific disease states.

Some of the compounds of general formula (I) are disclosed in U.S. Pat. Nos. 4,179,519 and 4,876,276. As disclosed in said U.S. patents, these essentially pure synthetic (+)—(3S,4S)-THC derivatives and analogues are devoid of any undesired cannabimimetic psychotropic side-effects. These known compounds have been described as having analgetic, antiemetic and antiglaucoma activity.

The inventors have now found that the said known compounds, as well as some novel compounds, in addition to having said analgetic, antiemetic and antiglaucoma activity, are also effective against the diseases and conditions mentioned above, possibly as excitatory amino acid receptor blockers, for example NMDA- or glutamate-blockers or interaction with the glycine receptor, and are effective in the alleviation and treatment of many of the abnormal states involving said neurotransmitters toxicity.

SUMMARY OF THE INVENTION

The present invention relates to pharmaceutical compositions adapted to reduce or even prevent I amino acids neurotoxicity, due to acute injury or poisoning of the CNS, such as injuries due to prolonged seizures, compromised or reduced blood supply, deprivation of glucose supply and mechanical trauma, and poisonings by, for example, strychnine, pycrotoxin or organophosphrous compounds poisonings.

The compositions of the present invention may also be effective in treating certain chronic degenerative diseases which are characterized by gradual selective neuronal loss. In this connection, the compositions of the present invention are contemplated as therapeutically effective in the treatment of Huntington's chorea, Parkinsonism disease and the Alzheimer's disease.

As stated above, the present compositions are of special value in seizures, global hypoxic ischemic insults, in hypoxia, alone or in combination with blood flow reduction (ischemia) as well as in cases of cardiac arrest and in cases of abrupt occlusion of cerebral arteries (stroke).

The present invention relates to pharmaceutical compositions for the purposes set out above, in which the active ingredient is a compound of the general formula:

(I)

having the (+)—(3S,4S) configuration, wherein A—B designates a 1(2) or a 6 (1) double bond, R designates CH₃ or CH₂OH, R¹ —designates a hydrogen atom or a lower acyl group, and R² designates (a) a straight-chained or branched $C_{6-12}$alkyl radical; or (B) a group —O—R³, in which R³ is a straight-chained or branched $C_{5-9}$alkyl radical or a straight-chained or branched alkyl radical substituted at the terminal carbon atom by a phenyl group.

In preferred compounds R² designates 1,1-dimethylalkyl radical or 1,2-dimethylalkyl radical with a total of at least 7 carbon atoms as well as precursors of such compounds.

Particularly preferred compounds are those wherein R² is 1,1-dimethylheptyl or 1,2-dimethylheptyl.

A preferred compound, with which many of the physiological experiments have been carried out is the compound (+)—(3S,4S)-1,1-dimethylheptyl homolog of 7-hydroxy-delta-⁶-tetrahydrocannabinol, designated hereafter as HU-211.

Experiments have shown that the (+)—(3S,4S) compounds of the formulae:

R = 1,1-DMH and

R = 1,1-DMH essentially free of the (—)—(3R,4R) enantiomer, wherein R² is 1,1-dimethylheptyl, have practically the same activity as that of the compound designated HU-211 (the compound of formula (II) is designated compound Vb in U.S. Pat. No. 4,179,517 and the compound of formula (IIa) is compound XIb therein).

In addition it has been found that some novel compounds of general formula (I), wherein R designates CH₂OH and R¹ designates a lower acyl group also have the desired anti-glutamate or glycine associated activity. These novel compounds may be prepared by acetylation of compounds of general formula (I) wherein R designates CH₂OH and R¹ is hydrogen, under conditions which favour the formation of this monoester with relatively high yield. Conventional esterification, for example, acetylation of the starting compound, which has two hydroxy moieties, using acetic anhydride and pyridine yields the diacetate, the monoacetate yield not exceeding 2–3%, which is of no practical synthetic value. Inventors have now found that by conducting the esterification with an acid anhydride in the presence of potassium 2-methyl-2-butoxide, under nitrogen atmosphere, esterification on the phenyl ring hydroxy group is preferred and the desired monoester is obtained in high yield.

Among the above novel compounds the monoacetate is preferred.

It is stressed that all the compounds are of the (+)—(3S,4S) configuration, essentially free of the (—)—(3R,4R) enantiomer, the latter known to possess the undesired psychotropic side-effects. Thus, as mentioned above, compounds of the type defined by general formula (I) are substantially devoid of "cannabis-type" CNS activity.

The novel compositions contain in addition to the active ingredient conventional pharmaceutically acceptable carriers, diluents and the like. Solid compositions for oral administration such as tablets, pills, capsules or the like may be prepared by mixing the active ingredient with conventional, pharmaceutically acceptable ingredients such as corn starch, lactose, sucrose, sorbitol, talc, stearic acid, magnesium stearate, dicalcium phosphate and gums with pharmaceutically acceptable diluents. The tablets or pills can be coated or otherwise compounded with pharmaceutically acceptable materials known in the art to provide a dosage form affording prolonged action or sustained release. Other solid compositions can be prepared as suppositories, for rectal administration. Liquid forms may may be prepared for oral or administration or for injection, the term including sub-cutaneous, transdermal, intravenous, intratechal, etc. administration. The liquid compositions include aqueous solutions, flavoured syrups, aqueous or oil suspensions, flavoured emulsions with edible oils, as well as elixirs and similar pharmaceutical vehicles. In addition, the compositions of the present invention may be formed as aerosols, for intranasal and like administration.

The active dose for humans is generally in the range of from 0.05 mg to about 50 mg per kg body weight, in regimen of 1–4 times a day. However, administration every two days may also be possible, as the drug has a rather prolonged action. The preferred range of dosage is from 1.0 mg to about 20 mg per kg body weight. However, it is evident to the man skilled in the art that dosages would be determined by the attending physician, according to the disease to be treated, method of administration, patient's age, weight, counterindications and the like.

All the compounds defined above are effective NMDA-receptor blockers and can be used as active ingredients of pharmaceutical compositions for treatment of one, or simultaneously several, of symptoms of the disorders defined above. The effective dosages are essentially similar, and the more pronounced effect is that of NMDA-receptor blocking, in addition to the known characteristics of these compounds. However, it is important to note that the compounds and compositions of the present invention exhibit good blocking activity also against convulsants which may not necessarily be NMDA-receptor blockers. For example the compositions of the present invention can prevent, or at least alleviate, poisoning caused by strychnine and NMDA.

The invention also relates to methods of treatment of the various pathological conditions described above, by administering to a patient a therapeutically effective amount of the compositions of the present invention. The term administration as used herein encompasses oral, parenteral, intravenous, intramuscular, sub-cutaneous, transdermal, intratechal, rectal and intranasal administration.

Figure 1:
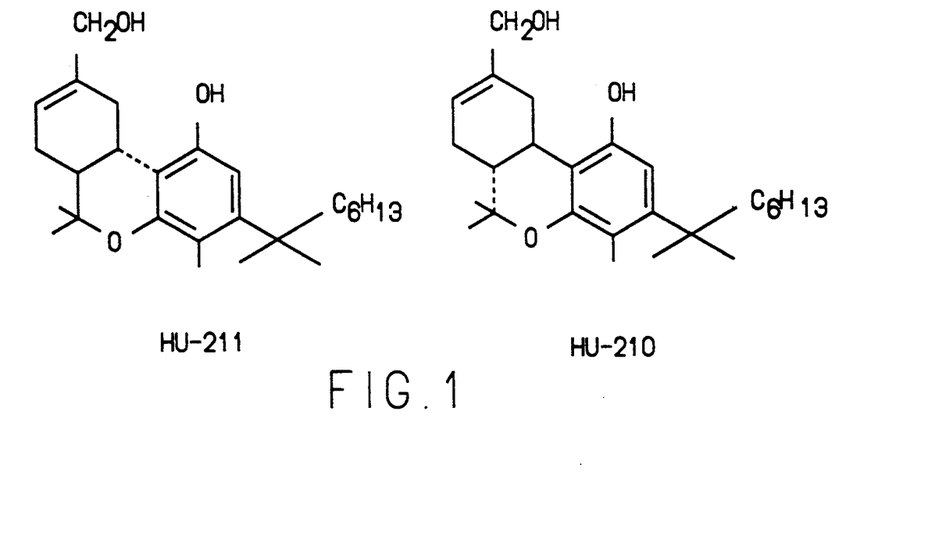
FIG. 1 gives the chemical structures of HU-210 and HU-211.

The enantiomers of the synthetic cannabinoid 7-hydroxy-delat-6-tetrahydro-cannabinol 1,1-dimethyl-heptyl homolog, have been described [Mechoulam, R., et al., Tetrahedron:Asymmetry 1, 315–319 (1990); Mechoulam, R. et al., Experientia 44: 762-764 (1988)]. The (−)—(3R,4R) enantiomer, herein designated HU-210 (see FIG. 1), is a highly potent cannabimimetic compound (nearly 100 times more active than delta-1-tetrahydrocannabinol, the active component of hashish). The (+)—(3S,4S) enantiomer, herein designated HU-211 (FIG. 1), while known to be active as an analgesic and as an anti-emetic, is inactive as a cannabimimetic even at doses several thousand times higher than the $ED_{50}$ of HU-210 [Mechoulam, R., et al., Experientia 44:762-764 (1988)].

The inventors have discovered that HU-211 and the compounds of formulae (II) and (IIa), as well as the said novel monoesters which are preferred active agents of the presently claimed compositions, at about 25 mg/kg body weight, induce stereotypy, locomotor hyperactivity and tachycardia effects typically caused by NMDA-receptor antagonists. At considerably lower doses of about 2.5 mg/kg body weight, they are potent blockers of NMDA-induced tremor, seizure and lethality. Thus, a good separation has been achieved between the therapeutic effects (NMDA antagonism) and possible side effects (such as tachycardia). Binding studies show that HU-211 blocks NMDA receptors in a stereospecific manner, and that the interaction occurs at binding sites distinct from those of other non-competitive NMDA antagonists or of glutamate and glycine. This, and the other compounds according to formula (I), may therefore prove useful as non-psychoactive drugs that protect against NMDA-receptor-mediated neurotoxicity.

As will be shown hereafter, the pharmacological profile of HU-211, and other compounds constituting the active ingredients of the present compositions, includes the induction of stereotypy, locomotor hyperactivity and tachycardia in mice (Table 1). These properties are consistent with those of non-competitive antagonists of the NMDA subclass of glutamate receptors, and suggest that these compounds are active NMDA-receptor antagonists. This possibility was explored by examining the activity of the compounds in protecting against the tremorogenic, convulsive and lethal efects of NMDA and NMDA agonists in mice. Such effects are counteracted by virtually all NMDA antagonists.

The invention will be described with reference to the following Figures and Examples.

BRIEF DESCRIPTION OF THE FIGURES

FIGS. 2 A–C illustrate the rate of binding of [$^3$H]TCP to the NMDA-receptor channel and the rate of dissociation of [$^3$H]TCP-receptor complexes;

PREPARATORY EXAMPLE

Potassium 2-methyl-butoxide (2 ml) was added to HU-211 (300 mg, 0.78 mmol) dissolved in benzene (30 ml). The solution was stirred, under $N_2$ atmosphere, for 45 min. Acetic anhydride (0.1 ml) was then added to the solution, followed by $NAHCO_3$ and water. The organic layer was dried over magnesium sulphate, filtered and evaporated. The crude reaction mixture was chromatographed on 15 g silica gel and eluted with 10%→30% ether:petrol ether solution to give:

Compounds a and b were reduced with $LiAlH_4$ to recover the starting material HU-211.

PHYSIOLOGICAL EXAMPLES

Example 1

The following is a comprehensive description of the experiments conducted in order to prove the desired inhibitory activity of the compositions of the present invention against NMDA-induced tremor, convulsion as well as lethality.

Sabra mice (an Israeli heterogenous strain) were pretreated with either vehicle alone (control) or HU-211 (1.25 or 2.50 mg/kg; s.c.), followed by NMDA (200 mg/kg; s.c.). As shown in Table 2, control and HU-211 pretreated animals showed significant differences with regard to the latency of tremor, latency of seizure, and time from NMDA injection until death. Similar experiments were performed using C-59 Black ice, in which the dose of NMDA was decreased (100 mg/kg; s.c.). Counteraction by Hu-211 of the NMDA-induced effects was more pronounced in the latter strain (which is more sensitive than Sabra mice to the effects of NMDA). In the control series of both strains, which received NMDA without HU-211, all animals died in less than 10 min. following seizure onset. In contrast, two of the five Sabra mice and six of the seven C-57 Black mice pretreated with HU-211 exhibited no tremors or seizures and stayed alive for more than four days following NMDA administration (Table 2). Preliminary results indicate that the anti-NMDA effects of HU-211 in C-57 Black mice persisted for more than 24 h. This was demonstrated by the marked alleviation of MMA-induced tremor and seizure and the continuing survival observed following the repeated administration of NDMA (100 mg/kg) one day later, in the six surviving C-57 Black mice. Taken together, these data provide compelling evidence that HU-211 is indeed an NMDA antagonist; moreover, since convulsion is a centrally-mediated phenomenon, the drug appears to exhibit a high degree of central penetration.

In order to identify the site of action of HU-211, a series of binding assays were conducted, using well-washed rat brain cortical membranes and the potent non-competitive blocker of the NMDA receptor, [$^3$H]-N-[1-(2-thienyl)-cyclohexyl]piperidine ([$^3$H]TCP) (40 Ci/mmol; 1 Ci=37 GBq; >98% pure, Israel Nuclear Research Center, Negev, Israel). With 100 μM HU-211 the equilibrium binding of 5 nm [$^3$H]TCP was not inhibited, suggesting that the behavioral effects of HU-211 are not exerted through non-competitive blocker site at the NMDA-receptor ion channel. Equilibrium binding experiments with 2-100 nM $^3$H)TCP in the presence of 1 μM glutamate and 1 μM glycine confirmed this suggestion: HU-211 (10 μM) did not alter the maximum binding capacity of [$^3$H]TCP (values recorded were 3.4 and 3.5 pmol/mg protein for controls and HU-211, respectively), and had no effect on the dissociation constant (Kd) for [$^3$H)TCP (27 nM for control and 26 nM for HU-211, respectively).

Figure 2A:
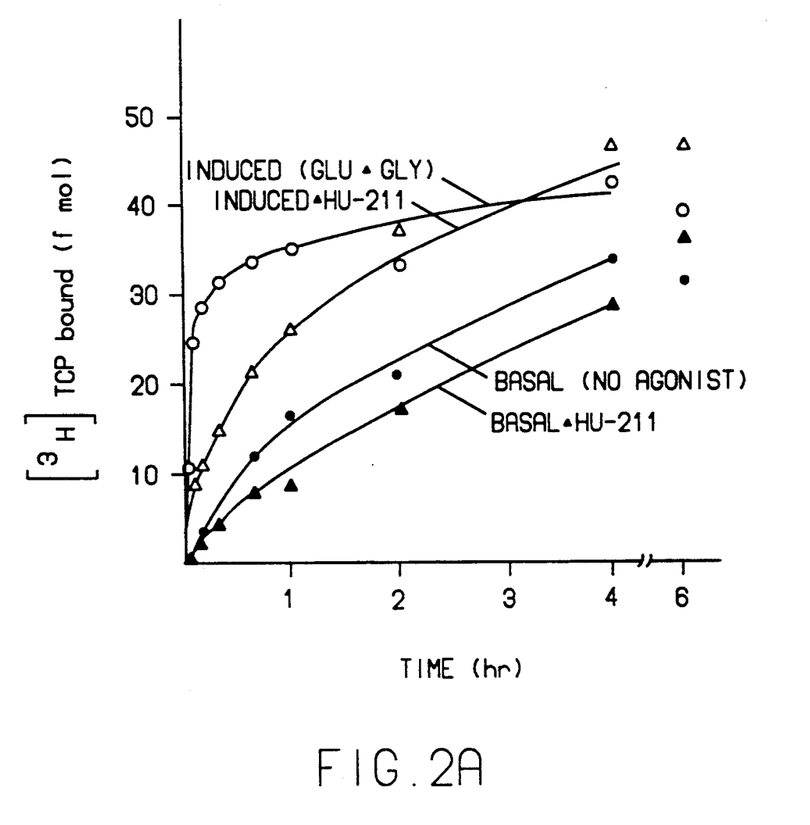

Kinetic experiments were then performed in order to determine whether HU-211 exerts its behavioral effects by acting directly at the glutamate- or the glycine-binding sites of the NMDA receptor. The use of this approach in previous studies, which were aimed at demonstrating the non-competitive nature of [$^3$H]TCP and [$^3$H]MK-801 ((+)-5-methyl-10,11-dihydro-5H-dibenzol[a,d]cyclohepten-5,10-imine maleate) binding to the NMDA receptor, showed that these compounds preferentially bind to the activated state of the receptor ion channel, and that glutamate and glycine accelerate the rates of association of non-competitive blockers to the receptor and their dissociation from it without altering their equilibrium binding. Results of the kinetic experiments with HU-211 are summarized in FIG. 2. As shown, the addition of 10 μM HU-211 resulted in only a small decrease in the rate of association of [$^3$H]TCP binding to the NMDA receptor, without altering the level of its equilibrium binding; in the presence of 1 μM glutamate and 1 μM glycine, however, the addition of 10 μHU-211 led to a marked decrease in the association rate (FIG. 2A). The addition of 10 μM HU-211 also decreased the dissociation rate of [$^3$H]TCP from the NMDA receptor, both in the absence and in the presence of 1 μM glutamate and 1 μM glycine, but much more strongly in their presence.

The kinetic data thus show that HU-211 acts functionally as an NMDA antagonist in the [$^3$H]TCP binding assay. Like the competitive NMDA antagonist aminophosphovalerate (AP-5), HU-211 reduces the glutamate/glycine potentiation of [$^3$H]TCP binding. However, unlike AP-5, which strongly inhibits [$^3$H]TCP binding even in the absence of glutamate and glycine (i.e., basal binding), HU-211 appears to be a much more active blocker of [$^3$H]TCP binding when glutamate and glycine are present (i.e., induced binding). This finding, as well as the marked structural differences between AP-5 and the cannabinoid, led to considering the possibility of whether the latter does not act at the glutamate or at the glycine site. Indeed it has been found that HU-211 (10 and 50 μM) reduced the efficacy of glutamate- or glycine-induced [$^3$H]TCP binding, but did not alter their apparent affinities (not shown). Taken together, the results suggest that HU-211 exerts at least some of its behavioral effects in animals by acting at a specific site of the NMDA receptor which is distinct from the binding sites for TCP, glutamate or glycine.

Several lines of evidence suggest that the effects of HU-211 on [$^3$H]TCP binding to the NMDA receptor are indeed exerted via a specific binding site rather than through non-specific perturbations of the membrane structure: (a) the effect on the initial rate of [$^3$HTCP binding is dose-dependent (FIG. 3), with an IC$_{50}$ value of 6-10 μM (IC$_{50}$=dose producing 50% inhibition of glutamate- or glycine-induced binding); (b) HU-211 is a far more potent inhibitor of the induced [$^3$H]TCP binding to the NMDA receptor than its (−)enantiomer HU-210 (FIG. 3), thus clearly pointing to stereospecific interaction between HU-211 and the NMDA receptor; (c) the IC$_{50}$ value for HU-211, determined under the same conditions but using phencyclidine/NMDA receptors solubilized with Na-cholate, was also 10 μM.

Recent evidence has indicated that brain damage induced by ischemia as well as by hypoglycemia is mediated, inter alia, by NMDA receptors. In light of the absence of psychotropic or other untoward side-effects seen after HU-211 administration, this drug merits serious consideration as drug of choice against NMDA-receptor-mediated neuropathologies, including epilepsy, Huntington's disease, and neuronal necrosis due to cerebral ischemia.

TABLE 1

A. Effects of HU-211 (2.5 mg/kg; s.c.) on induction of

TABLE 1-continued

| | stereotypy and locomotor activity in Sabra mice | | | | |
|---|---|---|---|---|---|
| | Time (min) | | | | |
| | 0 | 15 | 30 | 45 | 60 |
| Stereotypy Gradient | | | | | |
| Vehicle | 0.6 ± 0.2 | 0.5 ± 0.2 | 0.4 ± 0.2 | 0.3 ± 0.2 | 0.5 ± 0.3 |
| HU-211 | 0.4 ± 0.1 | 1.3 ± 0.2** | 2.2 ± 0.1** | 0.7 ± 0.2 | 0.6 ± 0.3 |
| Locomotor Activity | | | | | |
| Vehicle | 21.0 ± 6.0 | 20.0 ± 6.0 | 17.0 ± 10.0 | 6.0 ± 4.0 | 5.0 ± 3 |
| HU-211 | 32.0 ± 6.0 | 45.0 ± 2.0*** | 37.0 ± 4.0*** | 28.0 ± 13.0** | 17.0 ± 7 |

| B. Effect of HU-211 (2.5 mg/kg; s.c.) on induction of tachycardia in Sabra mice | | | |
|---|---|---|---|
| | Heart Rate (per min) | | |
| Time (min) | Vehicle | HU-211 | P |
| 0 | 170.3 ± 2.0 | 169.2 ± 2.5 | — |
| 75 | 171.0 ± 1.3 | 186.8 ± 2.5 | <.001 |

HU-211 was dissolved in ethanol and Emulphor 620, a non-ionic surfactant of a polyoxyethylene compound; double-distilled water was added so that ratio (by volume) in the final solution was 1:1:18. Six mice or rats were used in each experiment (including controls). Stereotypy was measured according to the stereotypy gradient SB gradient) of Feigenbaum et al., [*Pharmacol. Biochem. Behav.* 16:235–240 (1982)]. All animals were habituated for 45 min prior adminstration of of HU-211 or vehicle and tested 60 min following injection. Locomotor hyperactivity was measured as body displacement over 7-cm squares; movement from one square the next constituted a score of 1. Heart rate was measured 0 and 75 min following HU-211 injection. The student's t-test was used for statistical analysis of locomotor activity tachycardia. Since the SB gradient consists of discrete non-continuous scores, a non-parameter test (Mann Whitney U) was used.

$p<0.05$; $p<0.01$; *$p<0.001$. Values are means±SEM.

TABLE 2

| A. Inhibition by HU-211 of the tremorogenic effect of NMDA | | | | |
|---|---|---|---|---|
| Mouse strain | HU-211 dosage (mg/kg) | N | Time until first tremor (min) | P |
| Sabra | 0 | 6 | 2.6 ± 0.4 | |
| | 2.5 | 5 | 8.2 ± 1.3* | <0.001 |
| C-57 Black | 0 | 6 | 3.4 ± 0.4 | |
| | 1.25 | 5 | 12.0 ± 2.6* | <0.001 |
| | 2.50 | 7 | >4 days* | |

| B. Inhibition by HU-211 of the convulsive effect of NMDA | | | | |
|---|---|---|---|---|
| Mouse strain | HU-211 dosage (mg/kg) | N | Time until first seizure (min) | P |
| Sabra | 0 | 6 | 5.2 ± 1.6 | |
| | 2.5 | 5 | 18.0 ± 7.0 | <0.001 |
| C-57 Black | 0 | 6 | 6.5 ± 0.6 | |
| | 1.25 | 5 | 13.2 ± 2.6 | <0.001 |
| | 2.50 | 6 | 4 days* | |

| C. Inhibition by HU-211 of the lethal effect of NMDA | | | | |
|---|---|---|---|---|
| Mouse strain | HU-211 dosage (mg/kg) | N | Time until death (min) | P |
| Sabra | 0 | 6 | 9.3 ± 1.4 | |
| | 2.5 | 5 | 20.2 ± 7.0 | <0.001 |
| C 57 Black | 0 | 6 | 7.7 ± 0.8 | |
| | 1.25 | 5 | 18.6 ± 4.2 | <0.001 |
| | 2.50 | 7 | >4 days* | |

LEGEND TO TABLE 2

Hu-211 solution was prepared as described in Table 1. NMDA (Cambridge Research Biochemicals) was dissolved in double-distilled water. HU-211 was injected 75 min prior to NMDA administration. All injections were administered s.c. in volumes of 10 cc/kg body weight. Sabra mice were injected with 200 mg/kg NMDA and C-57 Black mice with 100 mg/kg NMDA.

* Two out of five animals pretreated with HU-211 did not exhibit tremor or seizure and stayed alive for more than 4 days. The number relates only to the remaining animals.

** Six out of seven animals stayed alive for more than 4 days and did not exhibit tremor or seizure; statistical analysis could therefore not be performed. Re-administration of NMDA (100 mg/kg) into these animals 24 h later also failed to induce tremor, seizure or death, and they stayed alive for at least 4 more days.

Values are means ±SEM.

The experiments described in Table 2 were repeated with C-57 Black mice, HU-211 replaced by the compound of formula (II) (compound Vb, U.S. Pat. No. 4,179,517) and the compound of formula (IIa)(compound XIb, ibid.). NMDA (100 mg/kg) was administered to the mice. At doses of 5 mk/kg the II and IIa compounds prevented the tremorogenic, convulsive and lethal effects in 4 out of 6 mice.

In addition, the experiments were repeated with the novel compound HU-247. HU-247 fully prevented the tremorogenic, convulsive and lethal effects of NMDA in 6 out of 7 C-57 Black mice, at doses of 2.5 mg/kg, under the same conditions described above.

Figure 2B:
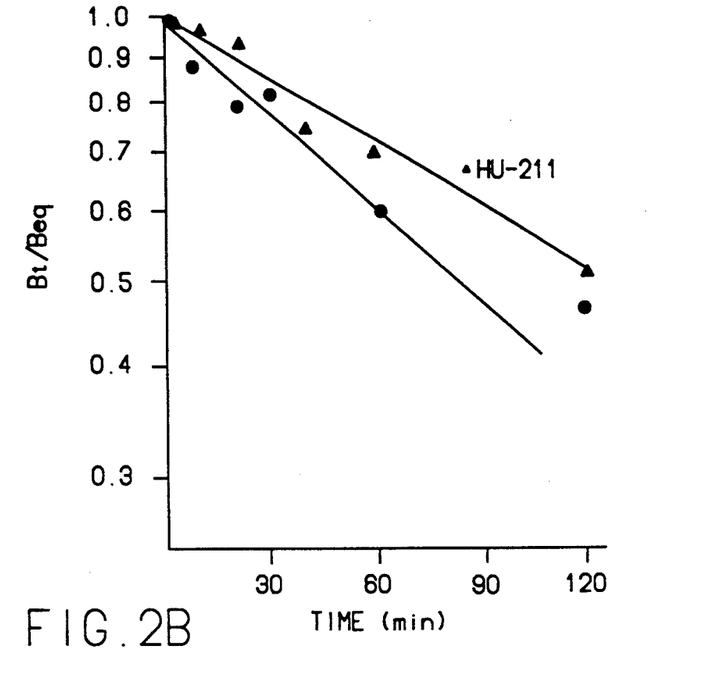
Figure 2C:
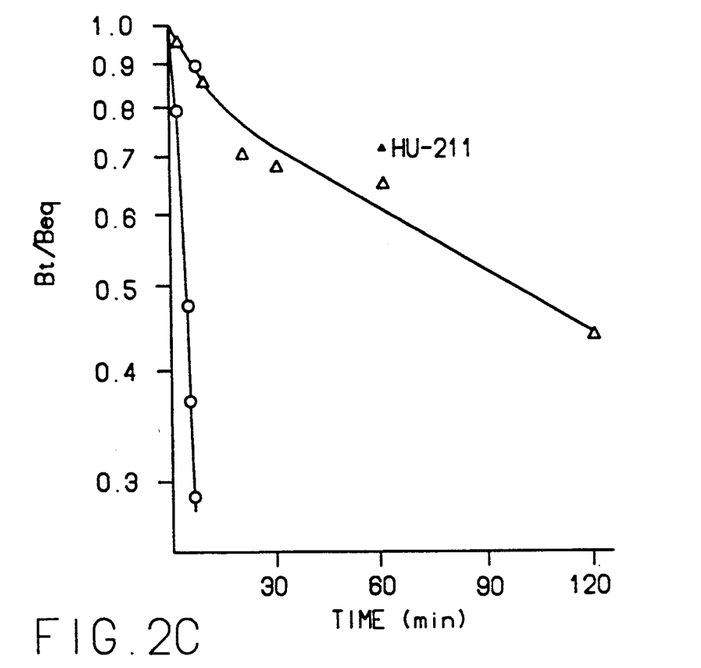

The results referred to as detailed in the Figures are as follows:

FIGS. 2 A–C

HU-211 reduces the rate of binding of [$^3$H]TCP to the NMDA-receptor channel and the rate of dissociation of [$^3$H]TCP-receptor complexes.

(A) Time course of basal (without added agonist) and induced (with 1 μM L-glutamate and 1 μM glycine) [$^3$H]TCP binding to the NMDA receptor of rat brain cortical membranes. Data represent the basal binding determined in the absence (o) and in the presence ( ) of 10 μM HU-211, and the induced binding determined in the absence (o) and in the presence ( ) of 10 μM HU-211. Binding of [$^3$H]TCP to well-washed control membranes was determined under the following conditions: membranes (80 μg protein) were incubated at 25° C. in 200 μl HEPES buffer, pH 7.4, containing 5 nM [$^3$H]TCP (total binding) or 5 nM [$^3$H]TCP and 100 μM PCP (phencyclidine) (nonspecific binding), and the reactions were terminated at the indicated times by rapid filtration over polyethyleneimine-treated GF/C filters. The filters were counted in scintillation liquid (Hydroluma, Lumac Inc., Netherlands). HU-211 was prepared as described elsewhere [Mechoulam, R., et al., Tetrahedron:Asymmetry, 1 315-319 (1990)). Means values (triplicates) of the specific binding of [$^3$H]TCP (total minus non-specific binding) are plotted as a function of the incubation time. The data shown are from one of three experiments that gave similar results.

(B-C) First-order plots of the basal (B) and the induced (C) dissociation of [$^3$H]TCP-receptor complexes. Data represent the basal (without added agonist) dissociation rates determined in the absence (o) and in the presence ( ) of 10 μM HU-211; the induced (with 1 μM L-glutamate and 1 μM glycine) dissociation rates were determined in the absence (o) and in the presence ( ) of 10 μM HU-211. Samples were preincubated as described for FIG. 2A, at 250° C. with 18 nM [$^3$H]TCP for 2 h. Basal dissociation reactions were initiated by the addition of 100 μM unlabeled PCP with or without 10 μM HU-211. For the induced dissociation reactions 1 μM glutamate and 1 μM glycine were also added. Reactions were terminated either immediately (zero time) or at the indicated times. B$_{eq}$, amount of [$^3$H]TCP bound at zero time. Bt, amount of [$^3$H]TCP boud at time t. The data shown are from one of three experiments, each performed in triplicate, that gave similar results.

Figure 3A:
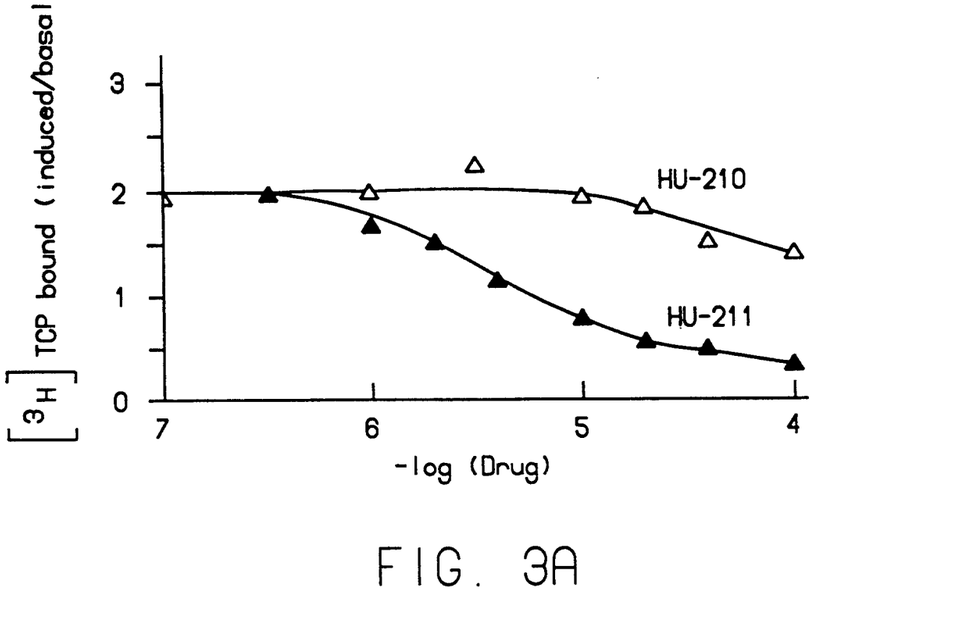
FIGS. 3A–B illustrate the stereoselective reduction of the rate of binding of [$^3$H]TCP to the NMDA receptor by HU-211.
Figure 3B:
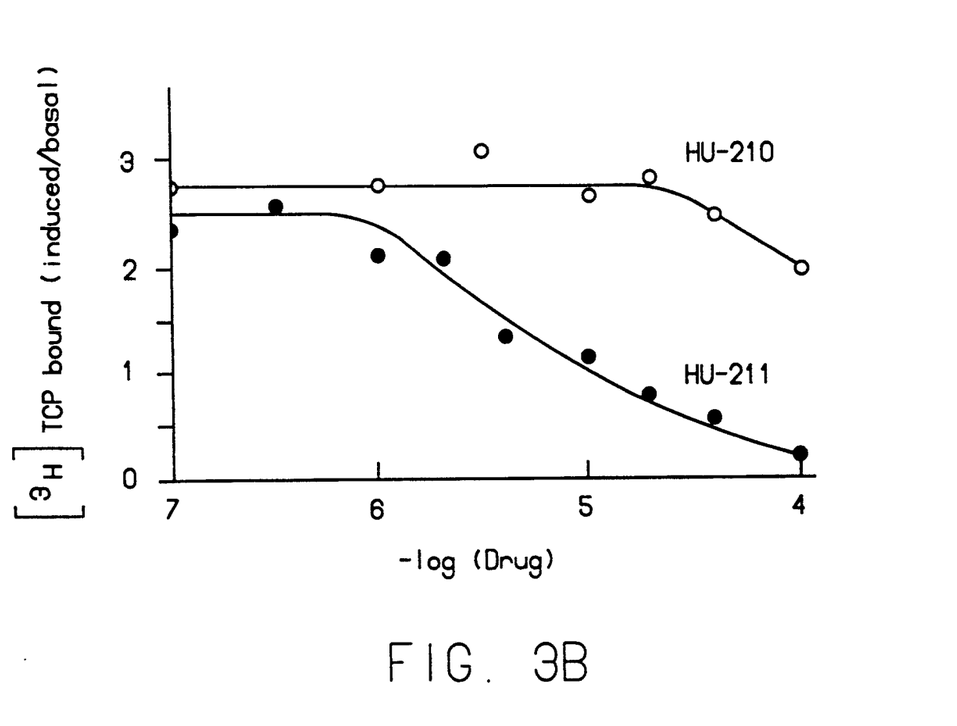

FIGS. 3 A-B

HU-211 reduces the rate of binding of [$^3$H]TCP to the NMDA receptor in a stereoselective manner.

Data represent the concentration-dependent decrease of [$^3$H]TCP binding by HU-211 (o) and by its isomer HU-210 (o). Binding of [$^3$H)TCP (5 nM) was determined as described for FIG. 2A, either in the absence (basal) or in the presence (induced) of 1 μM glutamate (A) or of 1 μM glycine (B).

Reactions were terminated after 10 min. Data are expressed as induced over basal binding as a function of isomer concentrations. Basal binding was 188 fmol/mg protein. Data are from one of two experiments that gave similar results.

Figure 4A:
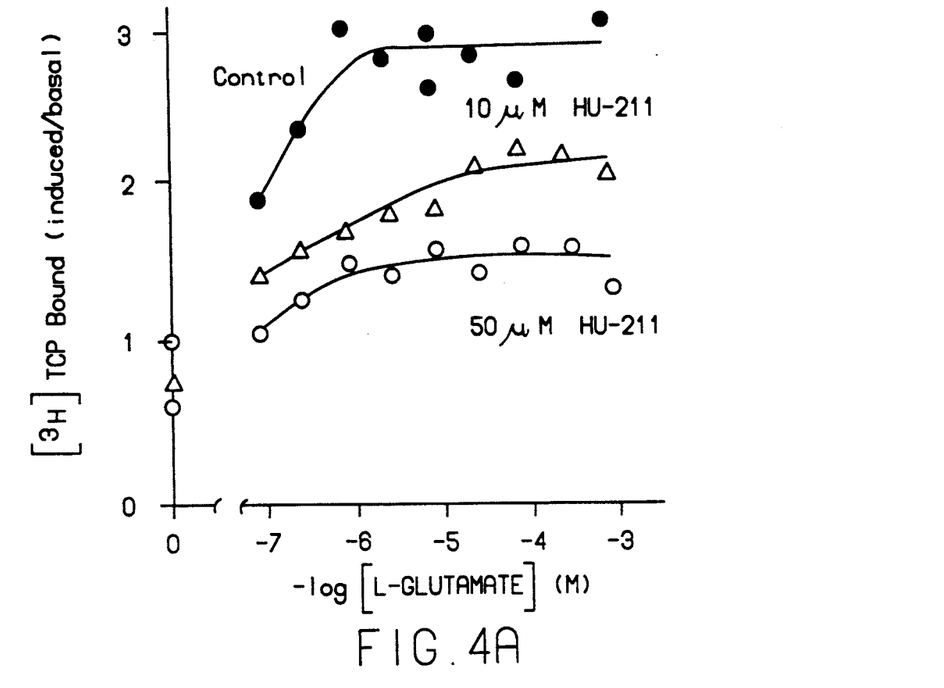
FIGS. 4A–B illustrate the non-competitive inhibition of glutamate- and glycine-induced [$^3$H]TCP binding by HU-211.
Figure 4B:
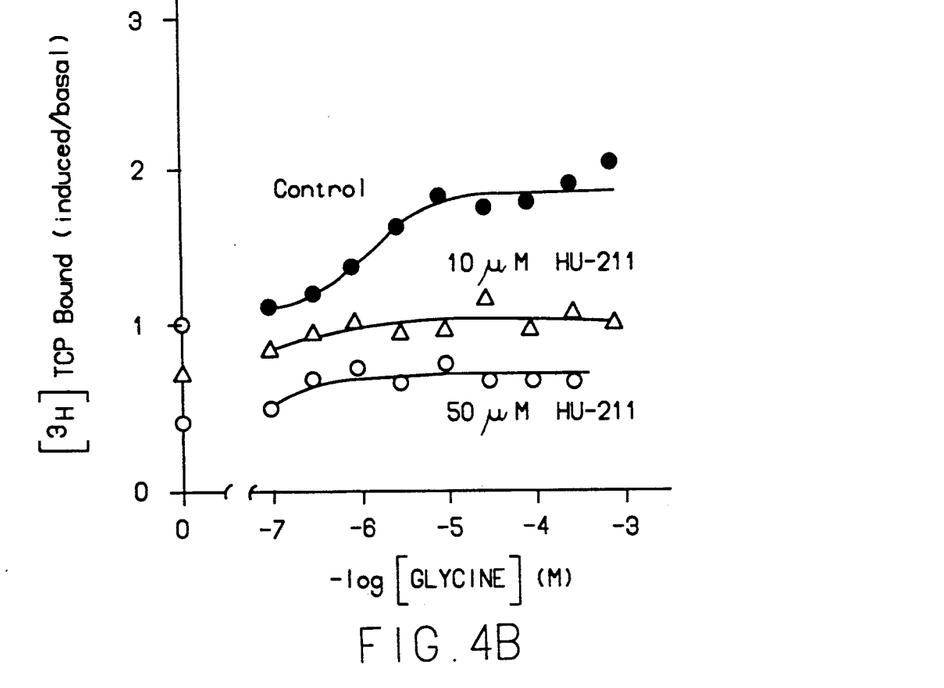

FIGS. 4 A-B

Non-competitive inhibition of glutamate- or glycine-induced [$^3$H]TCP binding by HU-211. Induced [$^3$H]TCP binding, corresponding to the ratio of binding in the presence of glutamate or glycine to binding in their absence, was determined with 5 nM [$^3$H]TCP at 25° C. for 10 min. Binding of ($^3$H)TCP to well-washed rat cortical membranes was determined in triplicate, as described previously [Kloog, Y., et al., Biochemistry, 27: 843-848 (1988)], in the absence (basal) and presence of various concentrations of L-glutamate (A) or glycine (B) with and without HU-211, as indicated. Data from one of two experiments that gave similar results.

EXAMPLE 2

Protection by HU-211 against picrotoxin, strychnine and NMDA toxicity.

BALB/C mice (20 g) were subcutaneously injected with picrotoxin, strychnine and NMDA in doses of about LD,, and subsequent clinical observations for the occurrence of convulsions and death were carried out within 20 min. The number of mice used and the mortality were assessed at the highest doses administered. Results are summarized in Table 3.

TABLE 3

| Toxin | Vehicle | Toxin Doses (mg/kg) | Time post HU-211 (min) | Doses of HU-211 (mg/kg) | Onset Time of clinical signs (min) | No. alive Total | % alive |
|---|---|---|---|---|---|---|---|
| NMDA | Emulphor | 125 | — | 0 | 8 | 0/10 | 0 |
| " | " | 125 | 120 | 5 | 19 | 2/10 | 20 |
| " | Emulsion | 125 | — | 0 | — | 1/7 | 14 |
| " | " | 125 | 120 | 5 | 7 | 4/7 | 60 |
| " | " | 125 | " | 10 | 10 | 8/10 | 80 |
| Str* | Emulphor | 1 | — | 0 | — | 0/10 | 0 |
| " | " | 1 | 75 | 10 | — | 8/10 | 80 |
| Pic** | Emulsion | 4 | — | 0 | 35 | 0/6 | 0 |
| " | " | 4 | 120 | 10 | 54 | 4/8 | 50 |

*Strychnine
**Picrotoxin

Emulphor—See I, Example 3
Emulsion—See II, Example 3.

As may be realized from the results presented in Table 3, HU-211 afforded better protection against NMDA toxicity when carried in the Emulsion (Example 3, II, hereafter) than in the Emulphor (Example 3, I) preparation.

EXAMPLE 3

Pharmaceutical Formulations

I. Emulphor

Active agents according to the invention, for example HU-211, were dissolved in ethanol/Finulphor 620 [GAF, USA]. Bidistilled water was added. Ratio of ethanol:Emulphor:water in final solution was 1:1:18.

In general, carriers of this type may be aqueous solutions comprising pharmaceutically acceptable cosolvents, such as, for example, ethanol, polyethyleneglycol, propylenegylcol, glycerol and the like. Within this context, carriers of this type may be micellar solutions prepared with natural or synthetic ionic or non-ionic surfactants. The carriers may also be combinations of these cosolvent and micellar solutions.

II. Emulsion

In some cases, pharmaceutical preparations in the form of emulsions comprising special ingredients, detailed hereafter, may be advantageous, as has been shown in Table 3.

These emulsions are prepared from an oily phase comprising pharmaceutically acceptable triglycerides, lecitine, stabilisers, antioxidants, in which phase the active compound is solubilized, and an aqueous phase containing glycerol and emulsifiers. Co-emulsifiers may optionally be added.

Each of the oily and aqueous phases are prepared separately, the phases are combined and stirred with a magnetic stirrer, while heated to 850° C. At this temperature a coarse emulsion is achieved, using a high shear mixer. After cooling, the coarse emulsion is homogenized, to give a fine emulsion. Finally, the pH is adjusted. Preserving agents such as parabens may be added.

Preferred triglycerides are medium- and long-chain triglycerides. Deoxycholate is a preferred stabiliser. α-Tocopherol is a preferred anti-oxidant. Pluronic F-68, a non-ionic surfactant of a copolymer of polyoxyethylene and polyoxypropylene, is a preferred emulsifier.

Thus, a general example of a desired formulation of an "Emulsion", referred to in Table 3 may be: triglycerides (from 1.0% to 30%, preferably 10%) lecithin (from 0.10% to 5%, preferably 1%), antioxidant, (% as required, according to specific anti-oxidant used) stabiliser (from 0.05% to 5%, preferably 1%), glycerol (% as required for isotonicity), emulsifier (from 0.20% to 10%, preferably 2%), active compound (from 0.05% to 5%) and water up to 100% (all % w/w).

Preserving agents such as parabens may be added (0.01–0.1%).

A typical formulation (% w/w): HU-211 (1.0) stabilized in oily phase (20.0), purified fractionated egg yolk phospholipids (1.2), Pluronic F-68 (2.0), glycerol (2.25), α-tocopherol (0.02), methyl-, butyl-p-hydroxybenzoic acid esters ( (0.2) and (0. 05) , respectively) and bidistilled water (up to 100).

We claim:

1. A method for treating injuries to the central nervous system due to cerebral ischemia or head trauma by administering to a patient a therapeutically effective amount of a compound of the formula I:

wherein A—B designates a 1(2) or 6(1) double bond, R is [lower alkyl of 1-3 carbon atoms] $CH_3$ or $CH_2OH$, $R^1$ is hydrogen or a lower acyl group and $R^2$ is (a) a straight or branched $C_6$–$C_{12}$ alkyl radical; (b) a group $OR^3$ in which $R^3$ is a straight or branched $C_5$–$C_9$ alkyl radical optionally substituted at the terminal carbon atom by a phenyl group, said formula having the (3S, 4S) configuration and being essentially free of the (3R, 4R) enantiomer.

2. The method of claim 1 wherein the compound of formula (I) is administered in a manner to protect against N-methyl-D-aspartate (NMDA) receptor mediated neurotoxicity.

3. The method of claim 1 which further comprises selecting the compound of formula (I) to be in the essentially pure (3S, 4S) form and having $R^1$ as a hydrogen atom and $R^2$ as 1,1-dimethylheptyl or 1,2-dimethylheptyl.

4. The method of claim 1 which further comprises selecting the compound of the formula (I) to have A—B as a 6(1) double bond, R as $CH_2OH$, $R^1$ as hydrogen and $R^2$ as 1,1-dimethylheptyl.

5. The method of claim 1 which further comprises administering the compound of formula (I) in the form of a pharmaceutical composition which includes a carrier or diluent.

6. The method of claim 5 which further comprises selecting the carrier or diluent to be an aqueous cosolvent solution comprising a pharmaceutically acceptable cosolvent, a micellar solution prepared with natural or synthetic ionic or non-ionic surfactants, or a combination of such cosolvent and micellar solutions.

7. The method of claim 5 which further comprises selecting the carrier to be a solution of ethanol, a surfactant and water.

8. The method of claim 5 which further comprises selecting the carrier to be an emulsion comprising triglycerides, lecithin, glycerol, an emulsifier, an antioxidant and water.

9. The method of claim 1 wherein the daily dosage of said compound of formula (I) is between about 0.05 and 50 mg/kg.

10. A method for blocking N-methyl-D-aspartate (NMDA) receptors in a patient which comprises administering to said patient a therapeutically effective amount of a compound of formula I wherein A—B designates a 1(2) or 6(1) double bond, R designates —$CH_3$ or $CH_2OH$, $R^1$ designates hydrogen or a lower acyl group and $R^2$ designates (A) a straight or branched $C_6$–$C_{12}$ alkyl radical; (B) a group —O—$R^3$, in which $R^3$ is a straight or branched $C_5$–$C_9$ alkyl radical optionally substituted at the terminal carbon atom by a phenyl group, said formula having the (3S,4S), configuration and being essentially free of the (3R,4R) enantiomer, said compound administered to block said receptors in a stereospecific manner.

11. The method of claim 10 wherein the compound of formula (I) is administered in a manner to protect against N-methyl-D-aspartate (NMDA) receptor mediated neurotoxicity.

12. The method of claim 10 which further comprises selecting the compound of formula (I) to be in the essentially pure (3S, 4S) form and having $R^1$ as a hydrogen atom and $R^2$ as 1,1-dimethylheptyl or 1,2-dimethyheptyl.

13. The method of claim 10 which further comprises selecting the compound of the formula (I) to have A—B as a 6(1) double bond, R as $CH_2OH$, $R^1$ as hydrogen and $R^2$ as 1,1-dimethylheptyl.

14. The method of claim 10 which further comprises administering the compound of formula (I) in the form of a pharmaceutical composition which includes a carrier or diluent.

15. The method of claim 14 which further comprises selecting the carrier or diluent to be an aqueous cosolvent solution comprising a pharmaceutically acceptable cosolvent, a micellar solution prepared with natural or synthetic ionic or non-ionic surfactants, or a combination of such cosolvent and micellar solutions.

16. The method of claim 14 which further comprises selecting the carrier to be a solution of ethanol, a surfactant and water.

17. The method of claim 14 which further comprises selecting the carrier to be an emulsion comprising a triglycerides, lecithin, glycerol, an emulsifier, an antioxidant and water.

18. The method of claim 10 wherein the daily dosage of said compound of formula (I) is between about 0.05 and 50 mg/kg.

* * * * *